(12) United States Patent
Schmidt et al.

(10) Patent No.: US 10,998,582 B2
(45) Date of Patent: May 4, 2021

(54) IMPROVING THE IONIC CONDUCTIVITY OF AN ELECTROLYTE BASED ON LITHIUM IMIDAZOLATE SALTS

(71) Applicants: Arkema France, Colombes (FR); Universite de Tours, Tours (FR)

(72) Inventors: Grégory Schmidt, Saint Andeol le Chateau (FR); Mérièm Anouti, St Avertin (FR); Daniel Lemordant, Pontcharra/Breda (FR); Laure Timperman, Esvres (FR); Christopher Berhaut, Lavausseau (FR)

(73) Assignee: ARKEMA FRANCE, Colombes (FR)

( * ) Notice: Subject to any disclaimer, the term of this patent is extended or adjusted under 35 U.S.C. 154(b) by 80 days.

(21) Appl. No.: 16/465,813

(22) PCT Filed: Nov. 30, 2017

(86) PCT No.: PCT/FR2017/053297
§ 371 (c)(1),
(2) Date: May 31, 2019

(87) PCT Pub. No.: WO2018/100297
PCT Pub. Date: Jun. 7, 2018

(65) Prior Publication Data
US 2019/0312309 A1     Oct. 10, 2019

(30) Foreign Application Priority Data
Dec. 2, 2016    (FR) ...................................... 1661855

(51) Int. Cl.
*H01M 10/056*     (2010.01)
*H01M 10/0568*    (2010.01)
(Continued)

(52) U.S. Cl.
CPC ...... *H01M 10/0568* (2013.01); *C07D 233/88* (2013.01); *H01M 10/052* (2013.01);
(Continued)

(58) Field of Classification Search
CPC ......... H01M 10/0567; H01M 10/0568; H01M 10/0569; C07D 233/88
See application file for complete search history.

(56) References Cited

U.S. PATENT DOCUMENTS 9,452,987 B2 * 9/2016 Armand ............ H01M 10/0525
9,722,277 B2 * 8/2017 Xiao ...................... H01M 4/38
(Continued)

FOREIGN PATENT DOCUMENTS

| CN | 104445133 A * | 3/2015 |
| WO | 2010023413 A1 | 3/2010 |
| WO | 2015136201 A1 | 9/2015 |

OTHER PUBLICATIONS

Machine translation of CN 104445133 (no date).*
(Continued)

*Primary Examiner* — Amanda C. Walke
(74) *Attorney, Agent, or Firm* — Buchanan Ingersoll & Rooney P.C.

(57) ABSTRACT

An electrolytic composition including at least one lithium salt of formula (A) wherein Rf represents a fluorine atom, a nitrile group, an optionally fluorinated or perfluorinated alkyl group having from 1 to 5 carbons, an optionally fluorinated or perfluorinated alkoxy group having from 1 to 5 carbons or an optionally fluorinated or perfluorinated oxa-alkoxy group having from 1 to 5 carbons; and the following solvent mixture: ethylene carbonate, γ-butyrolactone, and methyl propanoate. Also, to the use of the compositions in Li-ion batteries.

13 Claims, 4 Drawing Sheets

(51) Int. Cl.
*C07D 233/88* (2006.01)
*H01M 10/0525* (2010.01)
*H01M 10/0569* (2010.01)
*H01M 10/052* (2010.01)

(52) U.S. Cl.
CPC ... *H01M 10/0525* (2013.01); *H01M 10/0569* (2013.01); *H01M 2300/004* (2013.01); *Y02T 10/70* (2013.01)

(56) References Cited

U.S. PATENT DOCUMENTS

| | | | |
|---|---|---|---|
| 10,033,068 B2* | 7/2018 | Schmidt | H01M 10/0568 |
| 2011/0229769 A1 | 9/2011 | Ihara et al. | |
| 2011/0311884 A1 | 12/2011 | Armand et al. | |
| 2014/0295262 A1* | 10/2014 | Nakamoto | H01M 10/0568 |
| | | | 429/200 |
| 2015/0017551 A1* | 1/2015 | Schmidt | C07D 233/90 |
| | | | 429/326 |
| 2017/0025709 A1 | 1/2017 | Schmidt | |
| 2018/0034106 A1* | 2/2018 | Schmidt | H01M 10/0567 |
| 2018/0358658 A1* | 12/2018 | Gutel | H01M 10/0569 |
| 2019/0207246 A1* | 7/2019 | Dahn | H01M 10/0569 |
| 2020/0212488 A1* | 7/2020 | Schmidt | H01M 10/0567 |
| 2020/0259215 A1* | 8/2020 | Park | H01M 10/0568 |

OTHER PUBLICATIONS

International Search Report (PCT/ISA/210) and Written Opinion (PCT/ISA/237) dated Feb. 2, 2018, by the European Patent Office as the International Searching Authority for International Application No. PCT/FR2017/053297.

\* cited by examiner

IMPROVING THE IONIC CONDUCTIVITY OF AN ELECTROLYTE BASED ON LITHIUM IMIDAZOLATE SALTS

FIELD OF INVENTION

The present invention relates to an electrolytic composition comprising at least one electrolyte based on lithium imidazolate salts, and its use in Li-ion batteries.

The present invention also relates to the use of a mixture of specific solvents to improve the ionic conductivity of an electrolyte based on lithium imidazolate salts.

TECHNICAL BACKGROUND

A lithium-ion battery comprises at least a negative electrode (anode), a positive electrode (cathode), a separator and an electrolyte, said electrolyte generally consisting of a lithium salt dissolved in a solvent that is typically a mixture of organic carbonates, in order to have a good compromise between the viscosity and the dielectric constant.

Additives can be added to improve the stability of the electrolyte salts.

Among the most frequently-used salts is lithium hexafluorophosphate ($LiPF_6$), which has several of the numerous qualities required for use in batteries but presents the drawback of degrading into hydrogen fluoride gas by reaction with water and under the effect of temperature. This poses safety problems, in particular with regard to the use of lithium-ion batteries in private vehicles.

Recently, other salts have been developed, such as LiTDI (lithium 1-trifluoromethyl-4,5-dicarbonitrile-imidazolate) and LiPDI (lithium 1-pentafluoroethyl-4,5-dicarbonitrile-imidazolate). These salts have the advantage of having only 3 fluorine atoms which are strongly bonded to the carbon, thus less labile, instead of 6 fragile phosphorus-fluorine $LiPF_6$ bonds. These salts also have the advantage of not reacting with water to create hydrofluoric acid.

Moreover, document WO 2010/023413 shows that the conductivity of these salts is about 6 mS/cm, a very good dissociation between the imidazolate anion and the lithium cation. However, this ionic conductivity measured in "conventional" electrolyte solvents that are carbonate blends is too low to be used in "power" type batteries (for example, those used in tablet computers).

There is thus a need for new electrolyte compositions having high ionic conductivity, in particular based on lithium imidazolate.

DESCRIPTION OF THE INVENTION

Figure 1:
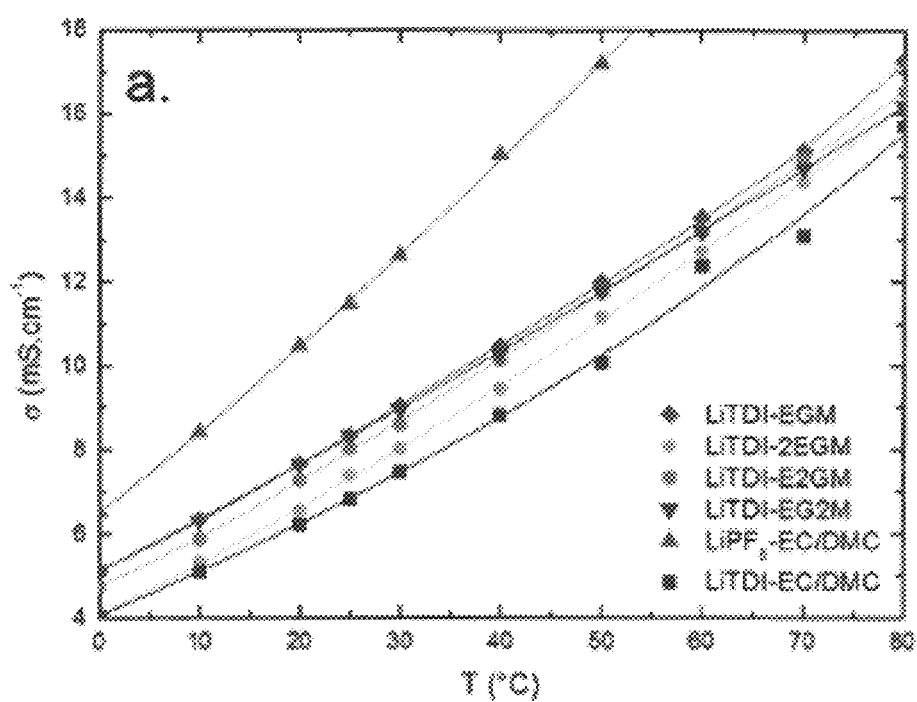
FIG. 1 shows the ionic conductivity relative to the temperature of the xEyGzM mixtures of Example 1 (with x, y and z representing the mass proportions of each solvent, E=ethylene carbonate, G=γ-butyrolactone, and M=methyl propanoate), in the presence of LiTDI at 1 mol/L.

The invention relates to an electrolytic composition comprising (preferably consisting of):
at least one lithium salt of formula (A):

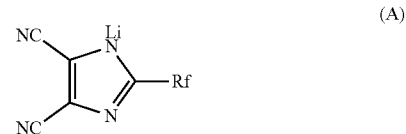

wherein Rf represents a fluorine atom, a nitrile group, an optionally fluorinated or perfluorinated alkyl group having from 1 to 5 carbons, an optionally fluorinated or perfluorinated alkoxy group having from 1 to 5 carbons or an optionally fluorinated or perfluorinated oxa-alkoxy group having from 1 to 5 carbons; and
the following solvent mixture: ethylene carbonate, γ-butyrolactone, and methyl propanoate ($CH_3CH_2COOCH_3$).

The applicant has discovered that the use of the ternary solvent mixture: ethylene carbonate/γ-butyrolactone/methyl propanoate advantageously makes it possible to improve the ionic conductivity of electrolytes based on lithium salts of formula (A), in particular based on LiTDI. The compositions according to the invention can be advantageously used as electrolytes in power type batteries.

Moreover, the low viscosity and broad temperature range at which the ternary mixtures according to the invention are in the liquid state advantageously offer a more extensive range of operating temperatures of the battery. The ternary mixture according to the invention advantageously enables the use of the salts of formula (A), and in particular lithium 2-trifluoromethyl-4,5-dicyano-imidazolate (LiTDI), in high- and medium-temperature applications.

According to the invention, the aforementioned electrolyte composition can comprise a salt of formula (A), or a mixture of salts of formula (A).

The following Rf groups can be mentioned as examples: F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_4F_9$, $C_4H_2F_7$, $C_4H_4F_5$, $C_5F_{11}$, $C_3F_5OCF_3$, $C_2F_4OCF_3$, $C_2H_2F_2OCF_3$, $CF_2OCF_3$, $CF_2OCH_3$, $C_5F_{11}OCH_3$, $CF_2OC_2H_5$, $CF_2OC_2H_4OCH_3$, $CF_2OC_2H_4OC_2H_5$, $CF_2OCH_2OCF_3$, $CF(CF_3)OCH_3$, $CF(CF_3)OC_2H_5$, $CF(CF_3)OC_2H_4OCH_3$ or $CF(CF_3)OC_2H_2F_3$.

Rf is preferably chosen from the group consisting of: F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_4F_9$, $C_4H_2F_7$, $C_4H_4F_5$ and $C_5F_{11}$.

Rf preferably represents a $CF_3$ group.

According to one embodiment, the mass content of ethylene carbonate is greater than 8%, preferably greater than 20%, advantageously greater than 25%, in particular greater than 30%, and preferentially greater than 45% of the total mass of the ternary mixture ethylene carbonate/γ-butyrolactone/methyl propanoate in the electrolytic composition.

According to one embodiment, the mass content of γ-butyrolactone is greater than 8%, preferably greater than 20%, advantageously greater than 25%, in particular greater than 30%, and preferentially greater than 45% of the total mass of the ternary mixture ethylene carbonate/γ-butyrolactone/methyl propanoate in the electrolytic composition.

According to one embodiment, the mass content of methyl propanoate is greater than 8%, preferably greater than 20%, advantageously greater than 25%, in particular greater than 30%, and preferentially greater than 45% of the total mass of the ternary mixture ethylene carbonate/γ-butyrolactone/methyl propanoate in the electrolytic composition.

According to the invention, the mass ratio of ethylene carbonate/γ-butyrolactone/methyl propanoate in the electrolytic composition can be comprised between 1/1/1 and 1/1/10 (preferably between 1/1/1 and 1/1/2), or between 1/1/1 and 1/10/1 (preferably between 1/1/1 and 1/2/1), or between 1/1/1 and 10/1/1 (preferably between 1/1/1 and 2/1/1).

According to one embodiment, the mass ratio of ethylene carbonate/γ-butyrolactone/methyl propanoate in the electrolytic composition is 1/1/1.

According to one embodiment, the mass ratio of ethylene carbonate/γ-butyrolactone/methyl propanoate in the electrolytic composition is 1/1/2.

According to one embodiment, the mass ratio of ethylene carbonate/γ-butyrolactone/methyl propanoate in the electrolytic composition is 1/2/1.

According to one embodiment, the mass ratio of ethylene carbonate/γ-butyrolactone/methyl propanoate in the electrolytic composition is 2/1/1.

According to one embodiment, the electrolytic composition comprises (preferably consists of):
at least one lithium salt of formula (A):

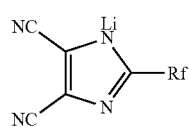

(A)

in which Rf is chosen among the group consisting of F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_4F_9$, $C_4H_2F_7$, $C_4H_4F_5$, $C_5F_{11}$, $C_3F_{50}OCF_3$, $C_2F_4OCF_3$, $C_2H_2F_2OCF_3$, $CF_2OCF_3$, $C_5F_{11}OCH_3$, $CF_2OC_2H_5$, $CF_2OC_2H_4OCH_3$, $CF_2OC_2H_4OC_2H_5$, $CF_2OCH_2OCF_3$, $CF(CF_3)OCH_3$, $CF(CF_3)OC_2H_5$, $CF(CF_3)OC_2H_4OCH_3$ and $CF(CF_3)OC_2H_2F_3$; preferably Rf is $CF_3$; and
the following solvent mixture: ethylene carbonate, γ-butyrolactone, and methyl propanoate, the (mass) ratio of ethylene carbonate/γ-butyrolactone/methyl propanoate in the electrolytic composition being preferably comprised between 1/1/1 and 1/1/10 (preferably between 1/1/1 and 1/1/2), or between 1/1/1 and 1/10/1 (preferably between 1/1/1 and 1/2/1), or between 1/1/1 and 10/1/1 (preferably between 1/1/1 and 2/1/1).

According to one embodiment, the concentration of lithium salt of formula (A) in the aforementioned electrolytic composition, in particular in which Rf represents $CF_3$, is comprised between 0.01 and 10 mol/L, preferably between 0.05 and 2 mol/L, preferentially between 0.1 and 1.5 mol/L, in particular between 0.5 and 1.2 mol/L, advantageously between 0.5 and 1 mol/L. Preferably, the concentration of lithium salt of formula (A) in the electrolytic composition, in particular in which Rf represents $CF_3$, is 1 mol/L.

The quantity of lithium salt of formula (A) dissolved in the solvent mixture above can vary between 0.01 and 10 mol/l, preferably between 0.05 and 2 mol/L, preferentially between 0.1 and 1.5 mol/L, and in particular between 0.5 and 1 mol/L.

Preferably, the lithium salt(s) of formula (A) represent between 2% and 100% by weight of all of the salts present in the electrolytic composition, preferably between 25% and 100% by weight, and preferentially between 50% and 100% by weight.

Preferably, the electrolytic composition does not comprise other lithium salts.

According to one embodiment, the mass proportion of lithium salt(s) of formula (A) in the electrolytic composition is comprised between 0.1% and 50%, preferably between 0.5% and 20% by mass respective to the total mass of the composition.

According to one embodiment, the mass proportion of the solvent mixture in the electrolytic composition is comprised between 20% and 99.9%, preferably between 50% and 99.5% by mass respective to the total mass of the composition.

The electrolytic composition according to the invention can comprise at least one additive, for example chosen in the group consisting of fluoroethylene carbonate (FEC), vinylene carbonate, 4-vinyl-1,3-dioxolan-2-one, pyridazine, vinyl pyridazine, quinoline, vinyl quinoline, butadiene, sebaconitrile, $LiB(C_2O_4)_2$, lithium nitrate, alkyl disulphides, fluorotoluene, 1,4-dimethoxy tetrafluorotoluene, tert-butylphenol, di-tert-butylphenol, tris(pentafluorophenyl)borane, oximes, aliphatic epoxides, halogenated biphenyls, metacrylic acids, allyl ethyl carbonate, vinyl acetate, divinyl adipate, acrylonitrile, 2-vinylpyridine, maleic anhydride, methyl cinnamate, phosphonates, silane compounds containing a vinyl, 2-cyanofurane, and mixtures thereof, the electrolytic additive preferably being fluoroethylene carbonate (FEC).

According to one embodiment, the electrolytic composition according to the invention can comprise additives, for example fluoroethylene carbonate or 1,3-Dioxol-2-one (vinylene carbonate).

The additive content in the electrolytic composition according to the invention can be comprised between 0.1% and 5%, preferably between 1% and 5% by mass respective to the total mass of the composition.

According to one embodiment, the electrolytic composition according to the invention has a kinematic viscosity greater than 1.5 mPa·s, preferably greater than 1.7 mPa·s, in particular comprised between 1.7 mPa·s and 6 mPa·s, at a temperature of 25° C.

The viscosity of the electrolytic composition can be measured at 25° C. using, preferably, an Anton Parr densimeter (for example model 60/602, Anton Parr, France) coupled with a ball viscometer (for example Lovis 2000/ME, Anton Parr, France) enabling the kinematic viscosity to be measured. The temperature of each device can be controlled with an uncertainty of ±0.02° C. For example, the densimeter can be previously calibrated with plain water provided for this purpose and dry air at atmospheric pressure, while distilled water can be used to calibrate the viscometer.

According to one embodiment, the electrolytic composition of the invention has an ionic conductivity greater than or equal to 7 mS/cm$^{-1}$, in particular comprised between 7 and 20 mS/cm$^{-1}$, at a temperature greater than or equal to 25° C. and preferably between 25° C. and 100° C., in particular between 25° C. and 80° C., the electrolytic composition preferably comprising a salt of formula (A) at a concentration of 1 mol/L.

In particular, the electrolytic composition according to the invention has an ionic conductivity greater than 7.5 mS/cm$^{-1}$, preferably greater than 8 mS/cm$^{-1}$, and preferentially greater than or equal to 8.5 mS/cm$^{-1}$ at 25° C.

The ionic conductivity can be measured by any known method. It can in particular be measured using a multi-frequency (1000-5000 Hz) Crison conductometer (GLP 31), or a multi-channel BioLogic conductometer composed of an impedance measurement module (MCM 10) connected to a Peltier module (WTSH 10) making it possible in particular to measure the conductivity between −40° C. and 150° C. The temperature measurements can be set by means of a thermostatically-controlled JULABO bath with an accuracy of 0.2° C.

Prior to each measurement, the conductivity cell can be calibrated, for example using KCl standard solutions at three different concentrations. The measurement cells consisting of parallel platinum electrodes can be sealed in a glove box that protects the samples from exposure to air and to any traces of humidity.

The present invention also relates to the use of said aforementioned electrolytic composition as an electrolyte in Li-ion batteries, in particular in Li-ion batteries for mobile device such as mobile telephones or laptop computers, for electric vehicles, and for the storage of renewable energy such as solar or wind energy.

Preferably, the present invention relates to the use of said aforementioned electrolytic composition as an electrolyte in Li-ion batteries (in particular in Li-ion batteries for mobile devices such as mobile telephones or laptop computers, for electric vehicles, and for the storage of renewable energy such as solar or wind energy) in a temperature range comprised between −60° C. and 130° C.

This application also relates to an electrochemical cell comprising a negative electron, a positive electron, and the electrolytic composition as described above, in particular interposed between the negative electrode and the positive electrode. The electrochemical cell can also comprise a separator, in which the electrolytic composition as defined above is impregnated.

The present invention also relates to a battery comprising at least one electrochemical cell as described above. If the battery comprises several electrochemical cells according to the invention, said cells can be assembled in series and/or in parallel.

Within the context of the invention, "negative electrode" means the electrode that acts as the anode when the battery is supplying current (i.e. when it is discharging) and that acts as a cathode when the battery is charging.

The negative electrode typically comprises an electrochemically active material, optionally an electron-conducting material, and optionally a binder.

Within the context of the invention, "electrochemically active material" means a material capable of reversibly inserting ions.

Within the context of the invention, "electron-conducting material" means a material capable of conducting electrons.

According to one embodiment, the negative electrode of the electrochemical cell comprises, as electrochemically active material, graphite, lithium, a lithium alloy, a lithium titanate of $Li_4Ti_5O_{12}$ or $TiO_2$ type, silicon or a lithium and silicon alloy, a tin oxide, an intermetallic lithium compound, or mixtures thereof.

The negative electrode can comprise lithium; the latter can then consist of a film of metallic lithium or of an alloy comprising lithium. An example of a negative electrode can comprise a film of active lithium prepared by lamination, between rollers, of a strip of lithium.

Within the context of the invention, "positive electrode" means the electrode that acts as the cathode when the battery is supplying current (i.e. when it is discharging) and that acts as an anode when the battery is charging.

The positive electrode typically comprises an electrochemically active material, optionally an electron-conducting material, and optionally a binder.

In another embodiment, the positive electrode of the electrochemical cell comprises an electrochemically active material chosen among manganese dioxide ($MnO_2$), iron oxide, copper oxide, nickel oxide, the lithium-manganese composite oxides (for example $Li_xMn_2O_4$ or $Li_xMnO_2$), the lithium-nickel oxide compositions (for example $Li_xNiO_2$), the lithium-cobalt oxide compositions (for example $Li_xCoO_2$), the lithium-nickel-cobalt composite oxides (for example $LiNi_{1-y}Co_yO_2$), the lithium-nickel-cobalt-manganese composite oxides (for example $LiNi_xMn_yCo_zO_2$ with x+y+z=1), the lithium-enriched lithium-nickel-cobalt-manganese composite oxides (for example $Li_{1+x}(NiMnCo)_{1-x}O_2$), the lithium and transition metal composite oxides, lithium-manganese-nickel composite oxides having a spinel structure (for example $Li_xMn_{2-y}Ni_yO_4$), the lithium-phosphorous oxides having an olivine structure (for example $Li_xFePO_4$, $Li_xFe_{1-y}Mn_yPO_4$ or $Li_xCoPO_4$), iron sulphate, the vanadium oxides, and mixtures thereof.

Preferably, the positive electrode comprises an electrochemically active material chosen among $LiCoO_2$, $LiFePO_4$ (LFP), $LiMn_xCo_yNi_zO_2$(NMC, with x+y+z=1), $LiFePO_4F$, $LiFeSO_4F$, $LiNiCoAlO_2$ and mixtures thereof.

The material of the positive electrode may also comprise, in addition to the electrochemically active material, an electron-conducting material as a source of carbon, including, for example, carbon black, Ketjen® carbon, Shawinigan carbon, graphite, graphene, carbon nanotubes, carbon fibres (such as vapour-grown carbon fibres (VGCFs), non-powdery carbon obtained by carbonisation of an organic precursor, or a combination of two or more thereof. Other additives may also be present in the material of the positive electrode, such as lithium salts or inorganic particles of ceramic or glass type, or other compatible active materials (e.g. sulphur).

The material of the positive electrode can also comprise a binder. Non-limiting examples of binders include linear, branched and/or crosslinked polyether polymer binders (for example, polymers based on poly(ethylene oxide) (PEO) or poly(propylene oxide) (PPO) or mixtures thereof (or an EO/PO co-polymer), and optionally comprising crosslinkable units)), water soluble binders (such as SBR (styrene-butadiene rubber), NBR (acrylonitrile-butadiene rubber), HNBR (hydrogenated NBR), CHR (epichlorohydrin rubber), ACM (acrylate rubber)), or fluorinated polymer type binders (such a PVDF (polyvinylidene fluoride), PTFE (polytetrafluoroethylene)), and combinations thereof. Some binders, such as the water-soluble ones, can also comprise an additive such as CMC (carboxymethyl cellulose).

The present invention also relates to the use of a mixture of solvents: ethylene carbonate, γ-butyrolactone, and methyl propanoate, to improve the ionic conductivity of an electrolyte based on lithium imidazolate salts, preferably salt of the aforementioned formula (A), and yet more preferably LiTDI (lithium 2-trifluoromethyl-4,5-dicyano-imidazolate) salt.

According to one embodiment, the invention relates to the use of a solvent mixture: ethylene carbonate, γ-butyrolactone, and methyl propanoate, to improve the ionic conductivity of an electrolyte based on lithium imidazolate salts, preferably salt of the aforementioned formula (A), in an Li-ion battery.

In the context of the invention, "comprised between x and y" or "ranging from x to y" refer to an interval in which the x and y limits are included. For example, the range "comprised between 25 and 100%" includes in particular the values 25 and 100%.

All the embodiments described above can be combined with each other.

The following examples illustrate the invention but without limiting it.

EXAMPLES

Example 1: Ionic Conductivity Measurements

Ionic conductivity was measured with two different instruments. The first was a multi-frequency (1000-5000 Hz) Crison conductometer (GLP 31). The temperature measurements were set by means of a thermostatically-controlled JULABO bath with an accuracy of 0.2° C. Prior to each measurement, the conductivity cell was calibrated using KCl standard solutions at three different concentrations. The second instrument used was a multi-channel BioLogic conductometer composed of an impedance measurement module (MCM 10) connected to a Peltier module (WTSH 10) making it possible to measure the conductivity between −40° C. and 150° C. The measurement cells consisting of parallel platinum electrodes were sealed in a glove box that protected the samples from exposure to air and to any traces of humidity.

FIG. 1 shows the ionic conductivity relative to the temperature of the xEyGzM mixtures (with x, y and z representing the mass proportions of each solvent, E=ethylene carbonate, G=γ-butyrolactone, and M=methyl propanoate), in the presence of LiTDI at 1 mol/L.

The electrolytic compositions according to the invention advantageously offer better ionic conductivity than LiDTI in a conventional ethylene carbonate (EC) and dimethyl carbonate (DMC) mixture.

In particular, a clear improvement in ionic conductivity was observed when switching from EC/DMC (mass ratio 1/1) to EGM (x=y=z=1, mass ratio 1/1/1) as the solvent mixture for LiTDI. Indeed, the conductivity of an LiTDI solution at 1 mol/L$^{-1}$ at 25° C. increased from 6.81 mS/cm$^{-1}$ in EC/DMC (mass ratio 1/1) to 8.32 mS/cm$^{-1}$ in EGM (x=y=z=1, mass ratio 1/1/1). For the temperature range studied herein, the LiTDI-EGM electrolyte (x=y=z=1, mass ratio 1/1/1) makes it possible in particular to obtain improved conductivity, closely followed by LiTDI-E2GM (x=z=1 and y=2, mass ratio 1/2/1) and LiTDI-EG2M (x=y=1 and z=2, mass ratio 1/1/2).

Due to its high relative permittivity (58±5) and its low viscosity in the presence of LiTDI at 1 mol/L$^{-1}$ (2.4 mPa·s at 25° C.), the EGM mixture (x=y=z=1, mass ratio 1/1/1) makes it possible to obtain greater conductivity for LiTDI (8.5 mS·cm$^{-1}$ at 25° C.) than the mixtures that have already been used in the presence of this lithium salt, such as EC/DMC (mass ratio 1/1) (6.8 mS/cm$^{-1}$), 3EC/7DEC (3.39 mS/cm$^{-1}$) (volume ratio 3/7) or 8EC/16DMC/1DME (mass ratio 8/16/1) (6.13 mS/cm$^{-1}$) (DEC and DME meaning, respectively, diethyl carbonate and dimethoxyethane).

Example 2: Viscosity

The kinematic viscosity of the compositions was measured at 25° C. using, preferably, an Anton Parr densimeter, model 60/602 (Anton Parr, France) coupled with a Lovis 2000/ME ball viscometer (Anton Parr, France). The densimeter was previously calibrated with plain water provided for this purpose and dry air at atmospheric pressure, whereas distilled water was used to calibrate the viscometer.

Figure 2:
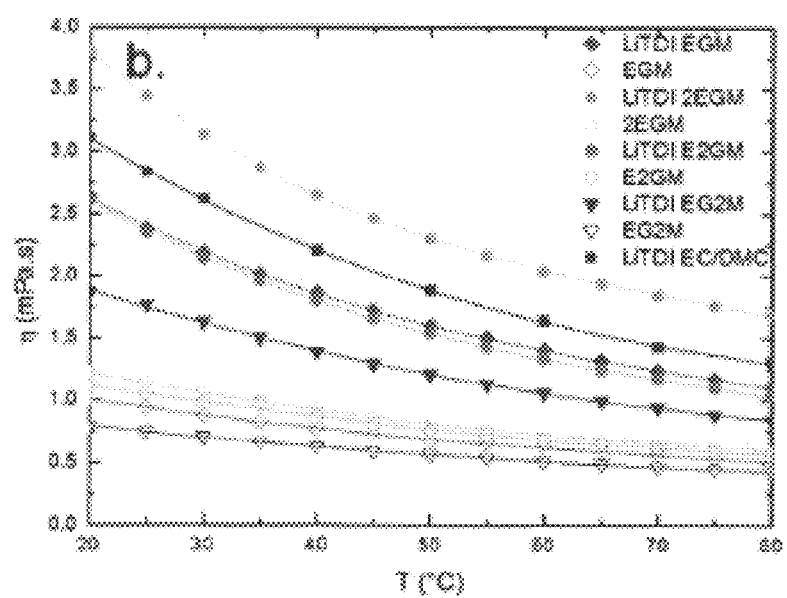
FIG. 2 shows the kinematic viscosity relative to the temperature, for the following compositions of Example 2: LiTDI-EGM, LiTDI-2EGM, EGM, 2EGM, LiTDI-E2GM, E2GM, LiTDI-EG2M, EG2M, LiTDI-EC/DMC.

FIG. 2 describes the kinematic viscosity relative to the temperature, for the following compositions: LiTDI-EGM, LiTDI-2EGM, EGM, 2EGM, LiTDI-E2GM, E2GM, LiTDI-EG2M, EG2M, LiTDI-EC/DMC.

Example 3: Differential Scanning Calorimetry

The results of the DSC (Differential Scanning Calorimetry) were obtained using the PerkinElmer DSC 4000. The samples, which were initially at 30° C., were first chilled to −40° C. then heated to 70° C. before being chilled again to −60° C., then finally heated to 150° C. Each scan was performed at 2° C./min$^{-1}$ and followed by an isotherm of 1 min.

Figure 3:
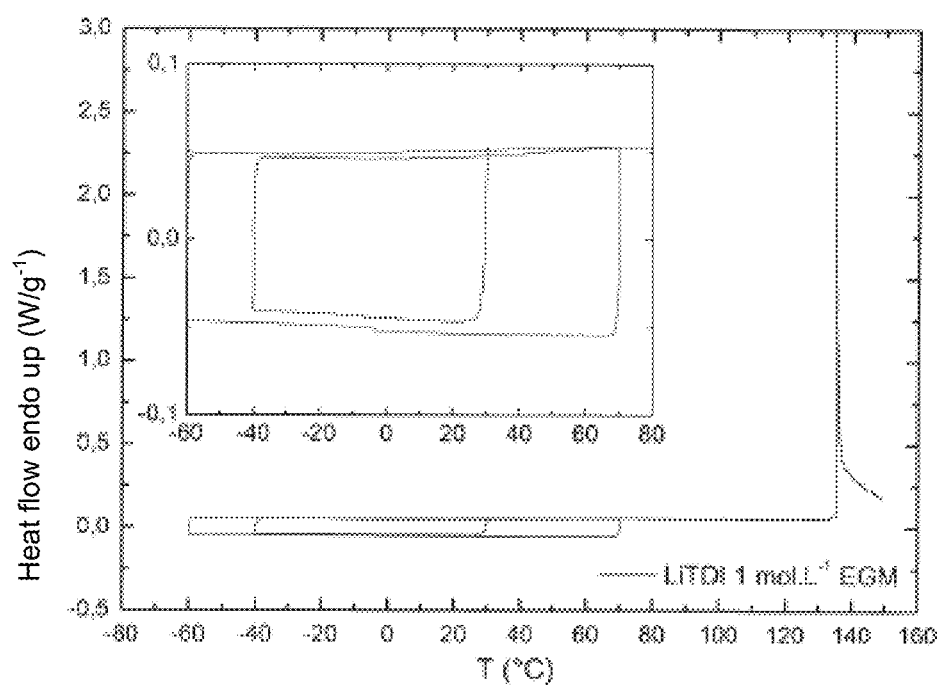
FIG. 3 shows a DSC thermogram of the LiTDI-EGM electrolyte of Example 3 (with LiTDI at a concentration of 1 mol/L), obtained at a scan speed of 2° C./min$^{-1}$.
Figure 4:
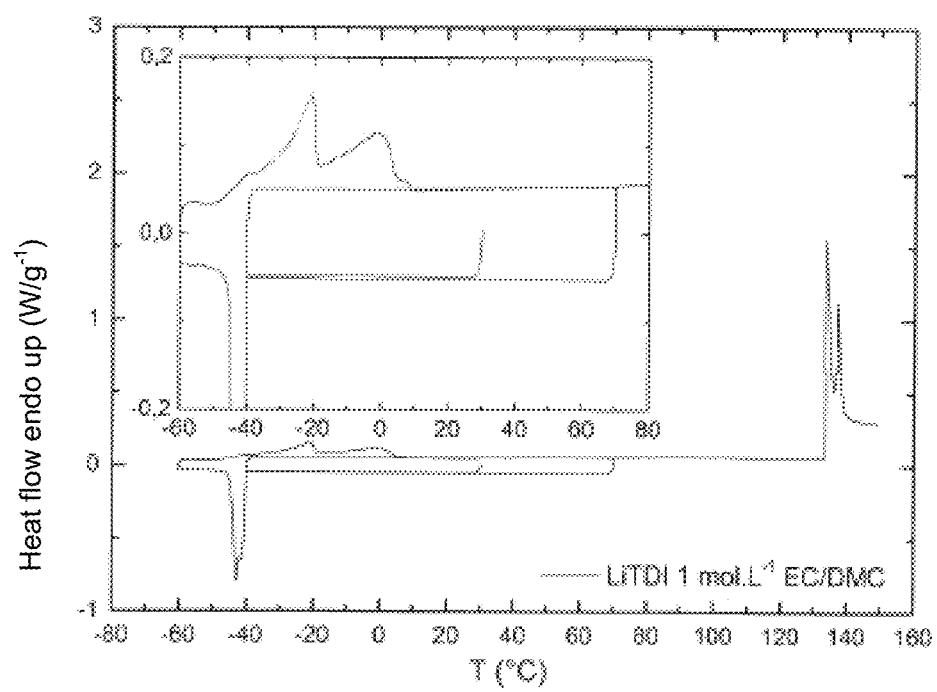
FIG. 4 shows a DSC thermogram of the LiTDI-EC/DMC electrolyte of Example 3 (with LiTDI at a concentration of 1 mol/L), obtained at a scan speed of 2° C./min$^{-1}$.

The DSC analyses between −60° C. and 150° C. of the LiTDI-EGM (1/1/1 by mass) (according to the invention) and LiTDI-EC/DMC (1/1) electrolytes (comparative example) are shown in FIGS. 3 and 4.

FIG. 3 is a DSC thermogram of the LiTDI-EGM electrolyte (with LiTDI at a concentration of 1 mol/L), obtained at a scan speed of 2° C./min$^{-1}$. The figure includes an enlargement of the temperature range between −60° C. and 80° C.

FIG. 4 is a DSC thermogram of the LiTDI-EC/DMC electrolyte (with LiTDI at a concentration of 1 mol/L), obtained at a scan speed of 2° C./min$^{-1}$. The figure includes an enlargement of the temperature range between −60° C. and 80° C.

Both electrolytes can withstand temperatures of up to about 130° C. Beyond that, the electrolytes start to boil, which causes the DCS capsules to burst. The LiTDI-EGM composition (mass ratio 1/1/1) (according to the invention) appears to be slightly more stable at high temperature. In spite of its volatility, the MP, in addition to the presence of GBL, allows for good behaviour of the LiTDI-EGM electrolyte (mass ratio 1/1/1) at very low temperature. Indeed, no change of phase was observed for the latter whereas the LiTDI-EC/DMC (comparison) solidified at −40° C. No solidification or melt peak was observed for the LiTDI-EGM (mass ratio 1/1/1) which suggests stability at lower temperatures.

The invention claimed is:
1. An electrolytic composition comprising:
   at least one lithium salt of formula (A):

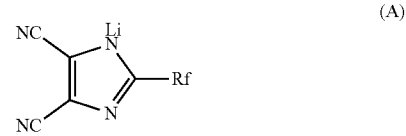

(A)

wherein Rf represents a fluorine atom, a nitrile group, an optionally fluorinated or perfluorinated alkyl group having from 1 to 5 carbons, an optionally fluorinated or perfluorinated alkoxy group having from 1 to 5 carbons or an optionally fluorinated or perfluorinated oxaalkoxy group having from 1 to 5 carbons; and
   the following solvent mixture: ethylene carbonate, γ-butyrolactone, and methyl propanoate, wherein the mass ratio of ethylene carbonate/γ-butyrolactone/methyl propanoate is between 1/1/1 and 1/1/10.

2. The composition according to claim 1, in which Rf represents F, $CF_3$, $CHF_2$, $CH_2F$, $C_2HF_4$, $C_2H_2F_3$, $C_2H_3F_2$, $C_2F_5$, $C_3F_5$, $C_3H_2F_5$, $C_3H_4F_3$, $C_4F_9$, $C_4H_2F_7$, $C_4H_4F_5$, $C_5F_{11}$, $C_3F_5OCF_3$, $C_2F_4OCF_3$, $C_2H_2F_2OCF_3$, $CF_2OCF_3$, $C_5F_{11}OCH_3$, $CF_2OC_2H_5$, $CF_2OC_2H_4OCH_3$, $CF_2OC_2H_4OC_2H_5$, $CF_2OCH_2OCF_3$, $CF(CF_3)OCH_3$, $CF(CF_3)OC_2H_5$, $CF(CF_3)OC_2H_4OCH_3$ or $CF(CF_3)OC_2H_2F_3$.

3. The composition according to claim 2, in which Rf represents $CF_3$.

4. The composition according to claim 1, in which the concentration of lithium salt of formula (A) in the composition is comprised between 0.01 and 10 mol/L.

5. The composition according to claim 1, in which the mass ratio of ethylene carbonate/γ-butyrolactone/methyl propanoate is 1/1/1 or 1/1/2.

6. The composition according to claim 1, wherein the composition possesses an ionic conductivity greater than or equal to 7 mS/cm$^{-1}$, at a temperature greater than or equal to 25° C.

7. The composition according to claim 1, wherein the composition possesses a kinematic viscosity of greater than 1.5 mPa·s, at a temperature of 25° C.

8. A Li-ion battery comprising a composition according to claim 1.

9. An electrochemical cell comprising a negative electron, a positive electron, and an electrolytic composition according to claim 1, preferably interposed between the negative electrode and the positive electrode.

10. A battery comprising at least one electrochemical cell according to claim 9.

11. A method of improving the ionic conductivity of an electrolyte based on lithium imidazolate salter, the method comprising adding a ternary solvent mixture: ethylene carbonate, γ-butyrolactone, and methyl propanoate, to an electrolyte based on lithium imidazolate salts, wherein the mass ratio of ethylene carbonate/γ-butyrolactone/methyl propanoate is between 1/1/1 and 1/1/10.

12. The method according to claim 11, wherein the addition is in a Li-ion battery.

13. An electrolytic composition comprising:
at least one lithium salt of formula (A):

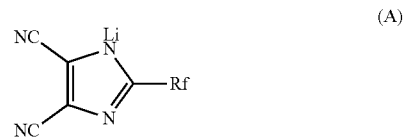

(A)

wherein Rf represents a fluorine atom, a nitrile group, an optionally fluorinated or perfluorinated alkyl group having from 1 to 5 carbons, an optionally fluorinated or perfluorinated alkoxy group having from 1 to 5 carbons or an optionally fluorinated or perfluorinated oxaalkoxy group having from 1 to 5 carbons; and
the following solvent mixture: ethylene carbonate, γ-butyrolactone, and methyl propanoate, wherein the mass ratio of ethylene carbonate/γ-butyrolactone/methyl propanoate is 1/2/1 or 2/1/1.

* * * * *

UNITED STATES PATENT AND TRADEMARK OFFICE
CERTIFICATE OF CORRECTION

PATENT NO. : 10,998,582 B2
APPLICATION NO. : 16/465813
DATED : May 4, 2021
INVENTOR(S) : Grégory Schmidt et al.

It is certified that error appears in the above-identified patent and that said Letters Patent is hereby corrected as shown below:

On the Title Page

At (73) Assignee: Please add, after "ARKEMA FRANCE, Colombes (FR)", the following:
--UNIVERSITE DE TOURS, Tours (FR)--

Signed and Sealed this
First Day of February, 2022

Drew Hirshfeld
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

Page 1 of 1

PATENT NO. : 10,998,582 B2
APPLICATION NO. : 16/465813
DATED : May 4, 2021
INVENTOR(S) : Grégory Schmidt et al.

It is certified that error appears in the above-identified patent and that said Letters Patent is hereby corrected as shown below:

On the Title Page

At (73) Assignee: Please add, after "ARKEMA FRANCE, Colombes (FR)", the following:
--UNIVERSITE DE TOURS, Tours (FR)--

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*